(12) United States Patent
Arakawa

(10) Patent No.: US 6,510,194 B1
(45) Date of Patent: Jan. 21, 2003

(54) METHOD AND APPARATUS FOR ACQUIRING TRANSMITTED-RADIATION IMAGE DATA

(75) Inventor: Satoshi Arakawa, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/472,441

(22) Filed: Dec. 27, 1999

(30) Foreign Application Priority Data

Dec. 25, 1998 (JP) .......................................... 10-370894

(51) Int. Cl.$^7$ .......................... A61B 6/00; G01N 23/00; G21K 1/12; H05G 1/60
(52) U.S. Cl. ............................................. 378/19; 378/4
(58) Field of Search ....................... 378/4, 19

(56) References Cited

U.S. PATENT DOCUMENTS

| | | | | |
|---|---|---|---|---|
| 4,891,833 A | * | 1/1990 | Bernardi | 378/145 |
| 5,319,693 A | * | 6/1994 | Eberhard et al. | 378/19 |
| 5,832,051 A | * | 11/1998 | Lutz | 378/8 |
| 5,848,114 A | | 12/1998 | Kawai et al. | 378/4 |

FOREIGN PATENT DOCUMENTS

JP          9-253079          9/1997 ............ A61B/6/03

OTHER PUBLICATIONS

"Cone–Beam CT—Present Status and Future Prospects", Image Information (M), pp. 122–127, Jan. 1988.
"Practical cone–beam algorithm", L.A. Feldkamp, L.C. Davis, J.W. Kress, J. Opt. Soc. Am. A/vol. 1, No. 6, Jun. 1984.
Handbook of Image Analysis, Tokyo Univ. Publn., pp. 356–371.

* cited by examiner

Primary Examiner—Drew A. Dunn
Assistant Examiner—Courtney Thomas
(74) Attorney, Agent, or Firm—Sughrue Mion, PLLC

(57) ABSTRACT

An entire detection area is divided into a plurality of division areas, and a single line sensor is disposed in each division area so that it is movable within each division area. While each line sensor is being moved within each division area by a moving unit, transmitted-radiation image data is acquired at each photographing position. The transmitted-radiation image data of the entire detection area is acquired by collecting the transmitted-radiation image data at the photographing positions.

16 Claims, 6 Drawing Sheets

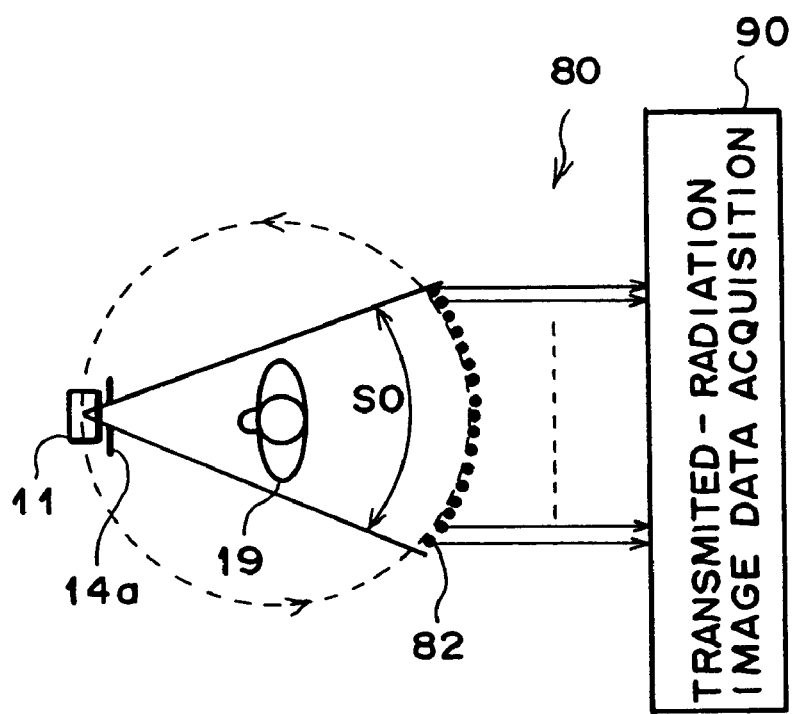
F I G. 6

METHOD AND APPARATUS FOR ACQUIRING TRANSMITTED-RADIATION IMAGE DATA

BACKGROUND OF THE INVENTION

1. Field of the Invention

The present invention relates to a method and apparatus for acquiring transmitted-radiation image data, and more particularly to a transmitted-radiation image data acquiring method and apparatus that is applied to a cone-beam computed tomograph (CT) which emits conical radiation to a subject in different directions of projection, acquires transmitted-radiation image data for each direction of projection, and generates volume data of the subject, based on the transmitted-radiation image data.

2. Description of the Related Art

In the field of medical imaging, research for detecting three-dimensional radiation image information has been undertaken. For example, a helical CT and a cone-beam CT have been proposed (see "Cone-Beam CT—Present Status and Future Prospects," Image Information (M), pp. 122–127, January 1988 and Japanese Unexamined Patent Publication No. 9(1997)-253079).

In the cone-beam CT, a radiation source and an area sensor (two-dimensional solid radiation detector) are disposed with a subject therebetween. While the radiation source and the area sensor are being rotated relatively with respect to the subject, conical radiation is emitted from the radiation source to the subject. The radiation transmitted through the subject is detected by the area sensor, whereby the transmitted-radiation image data of the subject is obtained at a different rotational position, i.e., for each direction of projection. Based on the obtained transmitted-radiation image data of the subject, the volume data of the subject is acquired. Based on the volume data of the subject, a three-dimensional image or a fault image is displayed on an image display such into as a CRT display, or the three-dimensional image or the like is temporarily stored in a storage device. Here, the solid radiation detector means a detector with a semiconductor device, which detects radiation and converts it to an electrical signal, as an essential part.

In the above-mentioned conventional cone-beam CT, incidentally, the area of a three-dimensional image or a fault image that can be displayed is an area which is formed by the overlapping portions in all directions of projection which the area sensor detects, specifically an inscribed circle of a total-radiation emitted area which is formed by conical radiation in each direction of projection that the area sensor can detect. That is, an image area that can be displayed is determined by the emission angle of radiation and the detection area of the area sensor. If the image area is enlarged, it will become necessary to emit conical radiation to the subject at a wider angle and to detect more of the wide-angle radiation transmitted through the subject with the area sensor. In other words, there is a need to employ a large-area sensor and to emit enough wide-angle radiation to cover the entire surface of the wide-area sensor to the subject.

However, it is difficult to fabricate a large-area sensor having a large detection area. Even if the sensor could be fabricated, it will be expensive, resulting in an increase in the cost of the cone-beam CT. For this reason, in the conventional cone-beam CT, it is difficult to display the image of a large area.

SUMMARY OF THE INVENTION

The present invention has been made in view of the aforementioned circumstances. Accordingly, it is an object of the present invention to provide a data acquiring method and apparatus which is capable of obtaining a large area quantity of transmitted-radiation image data without using a large-area sensor. Another object of the present invention is to provide a data acquiring method and apparatus that is capable of improving picture quality degradation due to scattered lines.

The first method according to the present invention is a method of acquiring transmitted-radiation image data on a subject, by emitting conical radiation from a radiation source toward the subject and by detecting the conical radiation transmitted through the subject with a solid radiation detector, while the radiation source and the solid radiation detector disposed with the subject therebetween are being rotated relatively with respect to the subject;

the method comprising the steps of employing a line sensor as the solid radiation detector; and obtaining an entire detection area quantity of transmitted-radiation image data by detecting the conical radiation transmitted through the subject with the line sensor, while the line sensor is being moved within the entire detection area for each direction of projection.

In the first method according to the present invention, an entire detection area quantity of transmitted-radiation image data is obtained by detecting the conical radiation transmitted through the subject with the line sensor, while the line sensor is being moved within the entire detection area for each direction of projection. Therefore, the detection area can be enlarged and it becomes possible to acquire a larger area quantity of transmitted-radiation image data without using a large-area sensor. If the present invention is applied to the cone-beam CT, it will become possible to display a three-dimensional image or a fault image of a larger area.

Here, the "entire detection area" means the entire range of a desired area to be obtained. For example, when it is assumed that an area sensor is used as the solid radiation detector, the "entire detection area" is equivalent to the entire detection area of the area sensor.

Detecting the radiation transmitted through the subject with the line sensor, while the line sensor is being moved within the entire detection area means that any method may be employed if detection is performed by moving the line sensor so that the sensor covers the entire detection area. For example, a single line sensor may be moved so that it covers the entire detection area. Alternatively, a plurality of line sensors may be moved so that each line sensor covers a predetermined range and movement of each line sensor may be added up in order to cover the entire detection area.

Note that in moving the line sensor, it is preferable to move the line sensor along a circular arc with respect to the radiation source. The same applies to the following description.

The second method according to the present invention is a method of acquiring transmitted-radiation image data on a subject, by emitting conical radiation from a radiation source toward the subject and by detecting the cone radiation transmitted through the subject with a solid radiation detector, while the radiation source and the solid radiation detector disposed with the subject therebetween are being rotated relatively with respect to the subject;

the method comprising the steps of employing a plurality of line sensors as the solid radiation detector;

dividing an entire detection area for each direction of projection into a plurality of division areas;

disposing each line sensor in each division area so that each line sensor is movable within the division area; and obtaining an entire detection area quantity of transmitted-radiation image data by detecting the conical radiation transmitted through the subject with each line sensor, while each line sensor is being moved within each division area.

In the second method according to the present invention, the entire detection area for each direction of projection is divided into a plurality of division areas. Each line sensor is disposed in each division area so that each line sensor is movable within the division area, and an entire detection area quantity of transmitted-radiation image data is obtained by detecting the conical radiation transmitted through the subject with each line sensor, while each line sensor is being moved within each division area. Therefore, as with the aforementioned first method and apparatus, it becomes possible to acquire a larger area quantity of transmitted-radiation image data, while the movable range of each line sensor is being reduced. In addition, it becomes possible to display a three-dimensional image or a fault image of a larger area.

The third method according to the present invention is a method of acquiring transmitted-radiation image data on a subject, by emitting conical radiation from a radiation source toward the subject and by detecting the conical radiation transmitted through the subject with a solid radiation detector, while the radiation source and the solid radiation detector disposed with the subject therebetween are being rotated relatively with respect to the subject;

the method comprising the steps of constituting the solid radiation detector by a plurality of line sensors arranged to cover an entire detection area; and obtaining an entire detection area quantity of transmitted-radiation image data by detecting the cone radiation transmitted through the subject with each line sensor.

In the third method according to the present invention, a plurality of line sensors arranged to cover an entire detection area are used as a solid radiation detector, and an entire detection area quantity of transmitted-radiation image data is obtained by detecting the conical radiation transmitted through the subject with each line sensor. Therefore, as with the aforementioned first method and apparatus, it becomes possible to acquire a larger area quantity of transmitted-radiation image data without moving each line sensor. In addition, it becomes possible to display a three-dimensional image or a fault image of a larger area.

Here, the "entire detection area" means an entire detection area for each direction of projection.

In either of the above-mentioned methods, it is preferable that substantially the rectilinear propagation component of the radiation, emitted from said radiation source and transmitted through said subject, be only incident on the line sensor (e.g., it is preferable to perform slit photographing). In this way, the influence of lines scattered at the subject can be suppressed.

In either method mentioned above, it is desirable to perform detection during the dilation period or contraction period of the heart in synchronization with the heartbeats of the subject. As a result, data can be obtained when the subject is substantially stationary. As a result, the image will not be obscure.

The first apparatus according to the present invention is an apparatus for acquiring transmitted-radiation image data on a subject, by emitting conical radiation from a radiation source toward the subject and by detecting the conical radiation transmitted through the subject with a solid radiation detector, while the radiation source and the solid radiation detector disposed with the subject therebetween are being rotated relatively with respect to the subject;

the apparatus comprising the radiation source;

a line sensor employed as the solid radiation detector;

means for moving the line sensor within an entire detection area for each direction of projection; and data acquiring means for acquiring an entire detection area quantity of transmitted-radiation image data by detecting the cone radiation transmitted through the subject with the line sensor at each moved position.

In the first apparatus according to the present invention, an entire detection area quantity of transmitted-radiation image data is obtained by detecting the conical radiation transmitted through the subject with the line sensor, while the line sensor is being moved within the entire detection area for each direction of projection. Therefore, the detection area can be enlarged and it becomes possible to acquire a larger area quantity of transmitted-radiation image data without using a large-area sensor. If the present invention is applied to the cone-beam CT, it will become possible to display a three-dimensional image or a fault image of a larger area.

The second apparatus according to the present invention is an apparatus for acquiring transmitted-radiation image data on a subject, by emitting conical radiation from a radiation source toward the subject and by detecting the conical radiation transmitted through the subject with a solid radiation detector, while the radiation source and the solid radiation detector disposed with the subject therebetween are being rotated relatively with respect to the subject;

the apparatus comprising the radiation source;

a plurality of line sensors employed as the solid radiation detector, each line sensor being disposed so that the line sensor is movable within each of a plurality of division areas formed by dividing an entire detection area;

means for moving each the line sensor within each division area for each direction of projection; and data acquisition means for acquiring an entire detection area quantity of transmitted-radiation image data by detecting the conical radiation transmitted through the subject with each the line sensor at each moved position.

In the second apparatus according to the present invention, the entire detection area for each direction of projection is divided into a plurality of division areas. Each line sensor is disposed in each division area so that each line sensor is movable within the division area, and an entire detection area quantity of transmitted-radiation image data is obtained by detecting the conical radiation transmitted through the subject with each line sensor, while each line sensor is being moved within each division area. Therefore, as with the aforementioned first method and apparatus, it becomes possible to acquire a larger area quantity of transmitted-radiation image data, while the movable range of each line sensor is being reduced. In addition, it becomes possible to display a three-dimensional image or a fault image of a larger area.

The third apparatus according to the present invention is an apparatus for acquiring transmitted-radiation image data on a subject, by emitting conical radiation from a radiation source toward the subject and by detecting the conical radiation transmitted through the subject with a solid radiation detector, while the radiation source and the solid radiation detector disposed with the subject therebetween are being rotated relatively with respect to the subject;

the apparatus comprising the radiation source;

a plurality of line sensors employed as the solid radiation detector, the plurality of line sensors being disposed to cover an entire detection area; and data acquisition means for acquiring an entire detection area quantity of transmitted-radiation image data by detecting the conical radiation transmitted through the subject with each the line sensor.

In the third apparatus according to the present invention, a plurality of line sensors arranged to cover an entire detection area are used as a solid radiation detector, and an entire detection area quantity of transmitted-radiation image data is obtained by detecting the conical radiation transmitted through the subject with each line sensor. Therefore, as with the aforementioned first method and apparatus, it becomes possible to acquire a larger area quantity of transmitted-radiation image data without moving each line sensor. In addition, it becomes possible to display a three-dimensional image or a fault image of a larger area.

In the aforementioned second and third data acquiring apparatuses, it is preferable that the line sensors be provided on a circular arc with respect to the radiation source. In this way, the distance between the radiation source and each line sensor can be made the same. Since no image distortion based on a difference in distance occurs, the correction of a magnification ratio becomes unnecessary.

In either apparatus mentioned above, it is also desirable to provide incident-direction control means, such as a slit and the like, which causes substantially the rectilinear propagation component of the radiation, emitted from the radiation source and transmitted through the subject, to be only incident on the line sensor. As a result, the influence of lines scattered at the subject can be suppressed.

In addition, it is desirable that the incident-direction control means be provided between the line sensors and the subject and between the radiation source and the subject. It is even desirable that the incident-direction control means be provided in circular arc form with respect to the radiation source.

Furthermore, it is desirable that either apparatus mentioned above be provided with synchronization means which performs detection during the dilation period or contraction period of the heart in synchronization with the heartbeats of the subject. In this way, data can be obtained when the subject is substantially stationary. As a result, the image will not be obscure.

In the aforementioned, the line sensor means a solid radiation detector with a narrow width and a long length. The line sensor is not limited to a one-dimensional solid sensor with a width equivalent to one pixel, but may be any sensor if it has a comparatively narrower width and a long length.

The above and many other objects, features and advantages of the present invention will become manifest to those skilled in the art upon making reference to the following detailed description and accompanying drawings in which preferred embodiments incorporating the principle of the present invention are shown by way of illustrative example.

BRIEF DESCRIPTION OF THE DRAWINGS

FIG. 6 is a schematic diagram of a data acquiring apparatus using a solid radiation detector constituted by a great number of line sensors.

DESCRIPTION OF THE PREFERRED EMBODIMENTS

Figure 1:
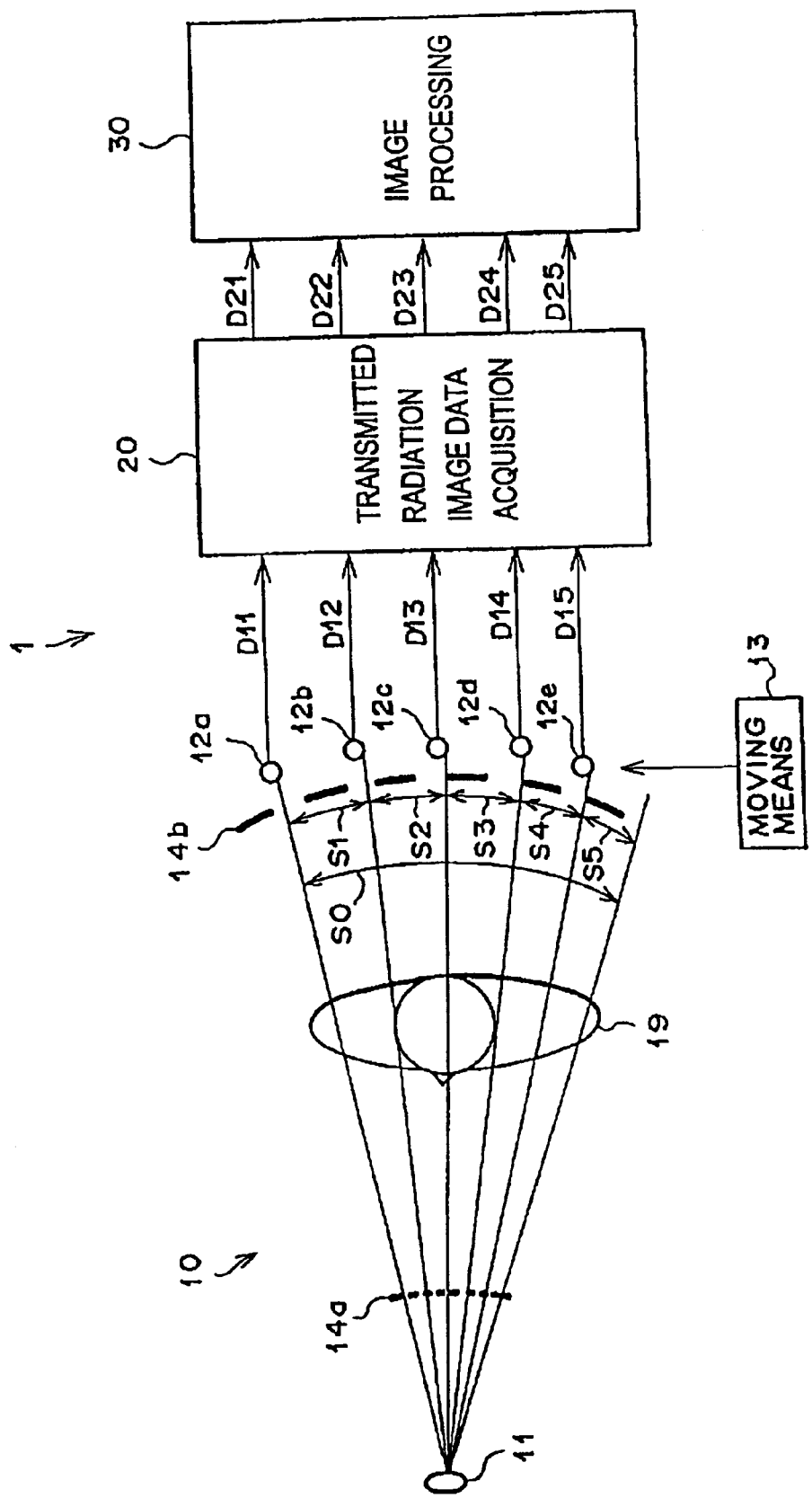
FIG. 1 is a schematic diagram showing a cone-beam CT utilizing a data acquiring apparatus with five line sensors constructed according to an embodiment of the present invention.

Referring to FIG. 1, there is shown a cone-beam CT to which a data acquiring apparatus according to an embodiment of the present invention is applied.

The cone-beam CT 1 includes a data acquiring apparatus 10 and an image processing section 30, as shown in FIG. 1. The data acquiring apparatus 10 comprises five line sensors 12a, 12b, 12c, 12d, 12e (referred to as a sensor 12 when collectively handled), moving means 13 which moves each line sensor 12, and data acquiring means 20 which generates transmitted-radiation image data, based on output of each line sensor 12. The image processing section 30 is connected to image display means (not shown) which displays and outputs a three-dimensional image or a fault image, formed by the image processing section 30, as a visible image. The "three-dimensional image" means a three-dimensional image that is viewed three-dimensionally from the viewpoint of vision (a three-dimensional image and a two-dimensional image that are viewed three-dimensionally from the viewpoint of vision).

Each line sensor 12 is a one-dimensional solid radiation detector. The entire detection area S0 is divided into five division areas S1 to S5. With respect to each direction of projection, each line sensor 12 is movable within each division area along a circular arc with respect to the radiation source 11. The line sensor 12 is disposed so that the longitudinal direction thereof becomes perpendicular to the paper surface.

The moving means 13 moves each line sensor 12 within each division area of the entire detection area S0 in accordance with a procedure to be described later, with respect to each direction of projection. The radiation transmitted through the subject 19 is detected at each moved photographing position by each line sensor 12.

The data acquiring means 20 generates transmitted-radiation image data D21 to D25, based on detection signals D11 to D12 from the line sensors 12. If the transmitted-radiation image data D21 to D25 at the photographing positions moved by the moving means 13 are collected, the collected data becomes transmitted-radiation image data covering the entire detection area S0, that is, an entire detection area quantity of transmitted-radiation image data.

The data acquiring apparatus 10 is provided with rotational control means (not shown) which relatively rotates the radiation source 11 and each line sensor 12 with respect to the subject 19. The rotational control means may be any type as long as it can sequentially switch the direction of projecting radiation over the entire circumference of the subject 19. For instance, the rotational control means may be a projection-system rotating type that rotates the radiation source 11 and the line sensor 12 with respect to the subject 19. Alternatively, it may be a subject rotating type that rotates the subject 19 on its center, while the radiation source 11 and the sensor 12 remain stationary.

The data acquiring apparatus 10 is further provided with incident-direction control means which controls the incident direction of radiation to each line sensor 12 in interlock with movement of the photographing position caused by the moving means 13 so that radiation making no contribution to detection is not emitted to the subject 19. The incident-direction control means comprises a first slit 14a disposed between the radiation source 11 and the subject 19 and a second slit 14b disposed between the subject 19 and the line sensors 12. Both slits 14a and 14b are provided in circular arc form with respect to the radiation source 11 so that substantially the rectilinear propagation component of the radiation, emitted from the radiation source 11 and transmitted through the subject 19, is only incident on each line sensor 12. It is preferable that movements of each line sensor 12 and slits 14a, 14b in a predetermined direction of projection be performed along a circular arm with respect to the radiation source 11. In this way, the influence of the lines scattered at the subject 19 can be eliminated, and since the radiation source 11 and each line sensor 12 can be moved with an equal distance maintained between them, correction of the magnification ratio becomes unnecessary. Note that it is a matter of course that the slits 14a, 14b are rotated relatively with respect to the subject 19 in synchronism with a change in the direction of projection.

The image processing section 30 obtains an entire detection area quantity of projection image data, volume data or the like, based on the entire detection area quantity of transmitted-radiation image data output from the data acquiring means 20. The "based on the entire detection area quantity of transmitted-radiation image data" means that the transmitted-radiation image data for each photographing position is synthesized for each photographing direction. A specific example of the synthesis will be described later.

Note that it is a matter of course that in using a plurality of line sensors in the aforementioned manner, if the characteristics differ from one another, then it is preferable to correct the characteristics so that equal data can be obtained.

The operation of the cone-beam CT 1 will hereinafter be described. Initially, a description will be given of the data acquiring apparatus 10.

The radiation source 11 and each line sensor 12 are first disposed in a predetermined direction of projection. Then, each line sensor 12 is disposed at a predetermined position within each division area. Next, the radiation source 11 emits conical radiation and the subject 19 is irradiated with the line radiation that has passed through the first slit 14a. The line radiation transmitted through the subject 19 is incident on each line sensor 12 via the second slit 14a. In this way, the sensors 12 output detection signals D11 to D15, respectively.

The data acquiring means 20 generates transmitted-radiation image data D21 to D25 corresponding to the photographing positions, based on the detection signals D11 to D15 from the line sensors 12.

Next, the line sensor 12 and slits 14a, 14b are moved slightly (preferably by an amount of 1 pixel) within each division area by the moving means 13. At the moved photographing positions, as with the aforementioned case, detection signals are obtained by the line sensors 12 and the data acquiring means 20 generates transmitted-radiation image data D21 to D25 corresponding to the moved photographing positions of the line sensors 12.

The same operation is repeated until each line sensor 12 covers the whole of each division area. If the transmitted-radiation image data D21 to D25 of the 5 division areas obtained by this repetition are added up, an entire detection area quantity of transmitted-radiation image data in the direction of projection is obtained. In this way, even if a large-area sensor is not used, the transmitted-radiation image data of a large detection area equal to the large-area sensor being used can be obtained. The obtained entire detection area quantity of transmitted-radiation image data D21 to D25 are input to the image processing section 30.

After an entire detection area quantity of transmitted-radiation image data D21 to D25 in a certain direction of projection have been obtained in the above-mentioned manner, the radiation source 11, each line sensor 12, and the slits 14a, 14b are rotated a predetermined amount with respect to the subject 19 by the rotational control means (not shown), with the relative position between them maintained. In this way, an entire detection area quantity of transmitted-radiation image data D21 to D25 in the direction of projection is obtained in the above-mentioned manner. This processing is repeated over 360 degrees, whereby an entire detection area quantity of transmitted-radiation image data is acquired for each direction of projection.

Note that the procedure of the operation between the movement of the liner sensor 12 within each division area in a predetermined direction of projection and the rotation to change the direction of projection is not limited to the above-mentioned example. For example, each line sensor 12 and the slits 14a, 14b are disposed at predetermined positions within each division area. While the radiation source 11, each line sensor 12, and the slits 14a, 14b are relatively being rotated 360 degrees with respect to the subject 19, the transmitted-radiation image data at the photographing positions may be obtained for each direction of projection. Thereafter, each line sensor 12 and the slits 14a, 14b may be moved slightly within each division area, and as with the aforementioned case, the transmitted-radiation image data at the photographing positions may be obtained, while each line sensor 12 and the like is being rotated.

Next, a description will be given of a method of forming the three-dimensional image or fault image of the subject 19, based on an entire detection area quantity of transmitted-radiation image data D21 to D25 in each direction of projection output from the data acquiring means 20.

Figure 2:
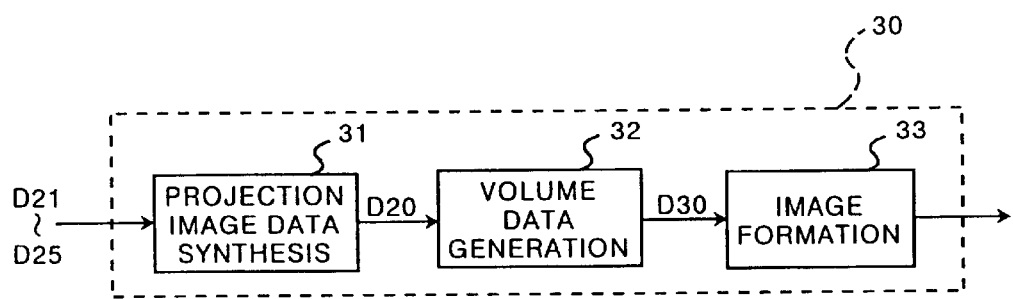
FIG. 2 is a block diagram showing an embodiment of the image processing section.

As shown in FIG. 2, the image processing section 30 includes projection image data synthesizing means 31, volume data generating means 32, and image forming means 33. The projection image data synthesizing means 31 performs various signal processing, such as γ correction and image distortion correction, on the entire detection area quantity of transmitted-radiation image data D21 to D25 input from the data acquiring means 20, for each direction of projection, and synthesizes the corrected image data D21 to D25, thereby generating a sheet quantity of synthesized projection image data D20 which covers the entire detection area.

In performing synthesis, an entire detection area quantity of transmitted-radiation image data D21 to D25 may first be synthesized to generate a sheet quantity of synthesized transmitted-radiation image data covering the entire detection area quantity. Then, based on the synthesized transmitted-radiation image data, synthesized projection image data may be generated. Alternatively, after each projection image data corresponding to each of the entire detection area quantities of transmitted-radiation image data has been generated, each projection image data may be synthesized to generate a sheet quantity of synthesized projection image data covering the entire detection area.

The volume data generating means 32 generates synthesized volume data D30 which covers the entire detection area by generating volume data, based on the synthesized projection image data D20. The image forming means 33 forms a three-dimensional image or a fault image, based on the synthesized volume data D30.

As an algorithm for volume data generation, a known calculation method of reconstituting three-dimensional data, such as Feldkamp algorithm (Feldkamp L A, Davis L C, Kress J W, "Practical cone-beam algorithm", J Opt Soc Am A 1984;1: pp. 612–619), a filter correction inverse projection method (Image Analysis Handbook (Tokyo University Publication), pp. 356–371) or the like, can be used. A detailed description of the method of generating the volume data is omitted (the same applies to the examples to be described later).

Thus, for each direction of projection, if the line sensor 12 is moved to cover the entire detection area in order to generate an entire detection area quantity of transmitted-radiation image data and if the entire detection area quantities of transmitted-radiation image data are synthesized to generate a sheet quantity of synthesized projection image data that covers the entire detection area then a large detection area quantity of transmitted-radiation image data equal to a single large-area sensor (which covers the entire detection area) being used can be generated, even if the large-area sensor is not used. As a result, it becomes possible to form a three-dimensional image or a fault image of a large image area.

In addition, transmitted-radiation image data can be acquired by disposing each photographing position on the same circumference with respect to the radiation source 11 so that the distances between the radiation source 11 and the line sensors 12 become the same. Therefore, an error due to a difference in distance between the radiation source 11 and the detecting position of the line sensor 12, that is, an error corresponding to a magnification ratio becomes smaller compared with the case of using a single large-area sensor.

Figure 3:
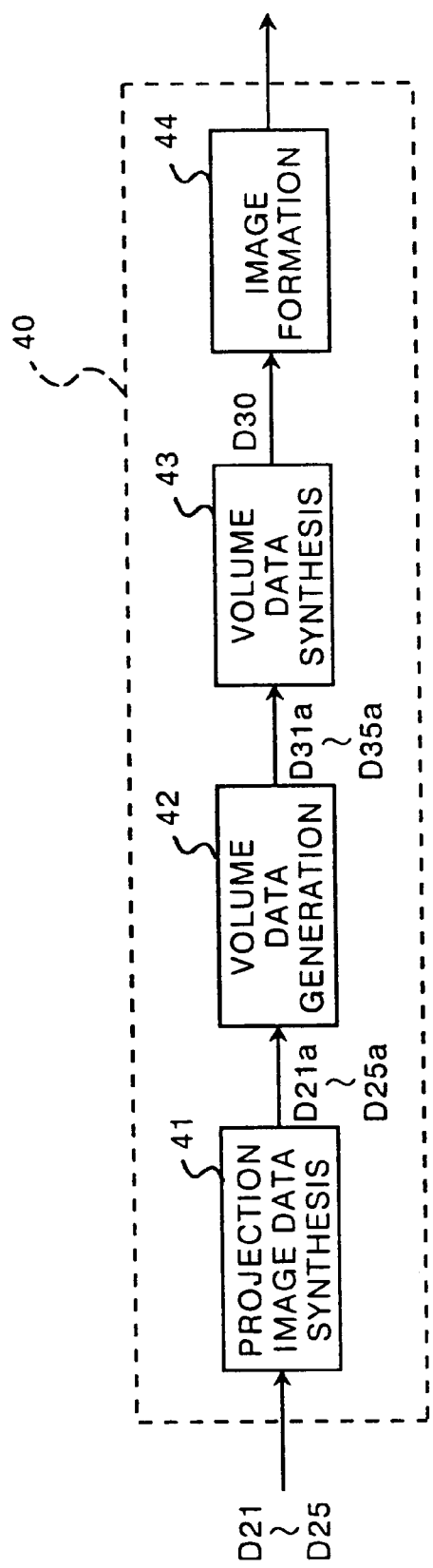
FIG. 3 is a block diagram showing another embodiment of the image processing section.

FIG. 3 shows an image processing section 40 employing another method of synthesis. This image processing section 40 includes projection image data synthesizing means 41, volume data generating means 42, volume data synthesizing means 43, and image forming means 44. The projection image data synthesizing means 41 generates the synthesized projection image data D21a to D25a of the 5 division areas, by synthesizing the transmitted-radiation image data D21 to D25 for each photographing position input from the data acquiring means 20, for each division area. Thus, the projection image data synthesizing means 41 differs from the above-mentioned projection image data synthesizing means 31 in that the projection image data synthesizing means 31 generates a sheet quantity of synthesized projection image data D20 which covers the entire detection area by synthesizing all the transmitted-radiation image data D21 to D25. The volume data generating means 42 generates the volume data D31a to D35a of the 5 division areas, based on the projection image data D21a to D25a of the 5 division areas. The volume data synthesizing means 43 synthesizes the volume data D31a to D35a, thereby generating a set of synthesized volume data D30 that covers the entire detection area. The image forming means 44 forms a three-dimensional image or a fault image, based on the synthesized volume data D30.

Thus, even when a set of synthesized volume data D30 that covers the entire detection area is generated, after the volume data D31a to D35a of the division areas have been generated by generating the synthesized projection image data D21a to D25a of the division areas, the image of a large area can be formed in the same manner as in the image processing section 30 shown in FIG. 2, without using a large-area sensor.

Figure 4:
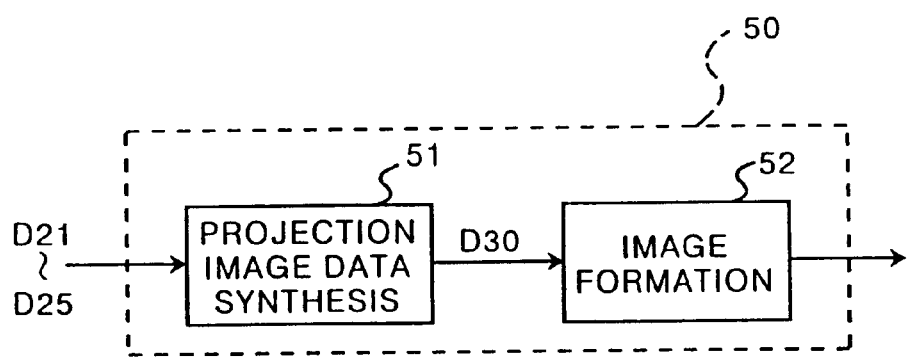
FIG. 4 is a block diagram showing still another embodiment of the image processing section.

FIG. 4 shows an image processing section 50 employing still another method of synthesis. This image processing section 50 includes volume data generating means 51 and image forming means 52. The volume data generating means 51 generates a set of synthesized volume data D30, which covers the entire detection area, immediately in the process of volume data generation, by generating volume data with the transmitted-radiation image data D21 to D25 for each photographing position input from the data generating means 20, for each direction of projection. In generating the volume data D30, each division area quantity of volume data may first be obtained and then synthesized, or an entire detection area quantity of volume data may be obtained at a time. The image forming means 52 forms a three-dimensional image or a fault image, based on the synthesized volume data D30.

Thus, even if the synthesized volume data is generated immediately in the process of volume data generation, the image of a large area can be formed in the same manner as in the image processing sections 30, 40, without using a large-area sensor.

Figure 5:
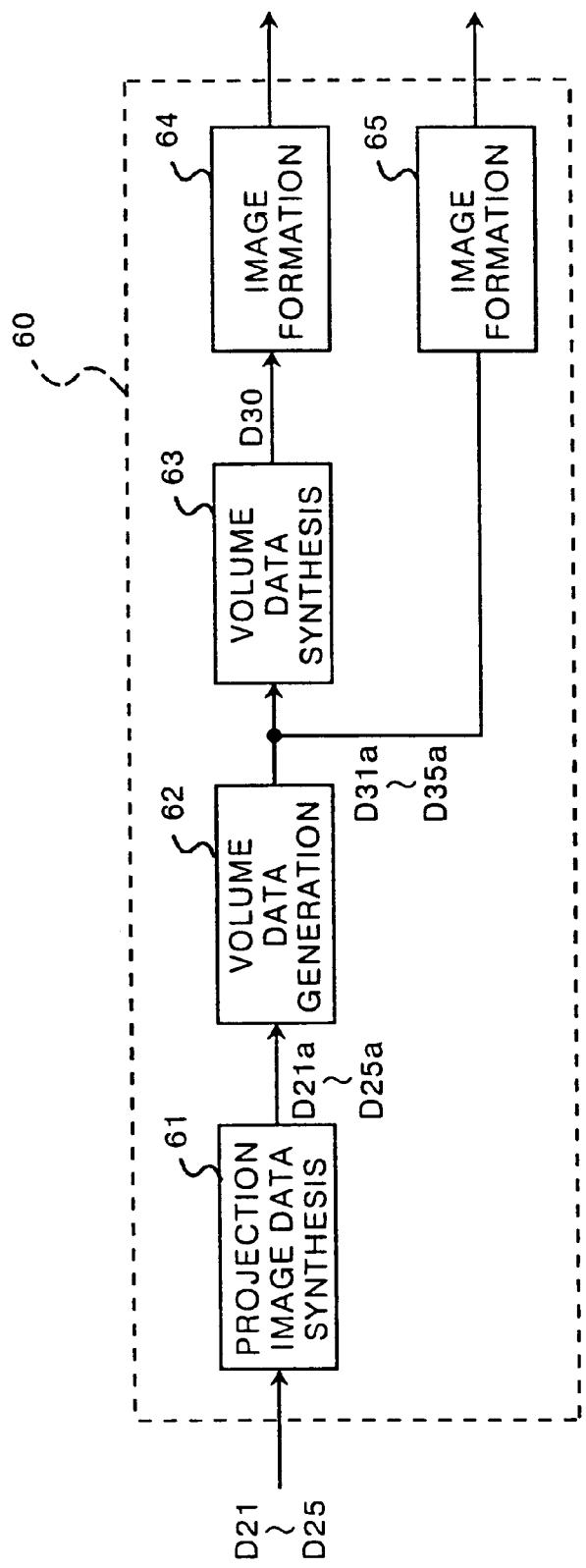
FIG. 5 is a block diagram showing a further embodiment of the image processing section.

FIG. 5 shows an image processing section 60 using a further method of synthesis.

This image processing section 60 includes projection image data synthesizing means 61, volume data generating means 62, volume data synthesizing means 63, first image forming means 64, and second image forming means 65. The image processing section 60 differs from the image processing section 40 of FIG. 3 in that the second image forming means 65 is further provided.

The first image forming means 64 shown in FIG. 5 performs only the operation of the image forming means 44 of FIG. 3 which forms a three-dimensional image. The second image forming means 65 forms a fault image for each division area, based on the volume data D31a to D35a of the division areas generated by the volume data generating means 42 and then forms a single synthesized fault image which covers the entire detection area by synthesizing the fault images.

Thus, even if a single synthesized fault image covering the entire detection area is formed, after a fault image has been formed for each division area, a large area quantity of fault image can be formed in the same manner as in the image processing section 30 and the like.

Incidentally, if an entire detection area quantity of transmitted-radiation image data is obtained by moving each line sensor in the above-mentioned way, the time for acquiring data will vary at each photographing position and therefore positional misalignment resulting from breathing or other body motion during that time will arise. Therefore, if the above-mentioned synthesizing process is performed based on transmitted-radiation image data including positional misalignment, three-dimensional positional misalignment will occur in an image based on various image data synthesized.

Therefore, it is desirable that positional alignment or image distortion correction employing data correlation be performed on at least the coupled portion between synthesized data in order to eliminate the positional misalignment.

If synchronization means for performing detection during the dilation period or contraction period of the heart in synchronization with the heartbeats of the subject 19 is provided for obtaining data when the subject 19 is substantially stationary, positional misalignment can be eliminated without performing positional alignment or image distortion correction.

In the above-mentioned embodiment, a plurality of line sensors are employed and each line sensor is moved within each division area to cover each division area. The transmitted-radiation image data obtained by movement of each line sensor are synthesized (or added up), whereby the transmitted-radiation image data covering the entire detection area is acquired. However, the present invention is not necessarily limited to this embodiment, but is able to employ any method as long as the line sensor is moved to cover the entire detection area.

For instance, an entire detection area quantity of transmitted-radiation image data may be acquired by moving a single line sensor so that the entire detection area is covered, and by adding up the transmitted-radiation image at each photographing position obtained by the movement of the single line sensor.

Now, a description will be given of a method and apparatus for acquiring transmitted-radiation image data, according to a second embodiment of the present invention. FIG. 6 shows the data acquiring apparatus 80 according to the second embodiment of the present invention. The data acquiring apparatus 80, as with the above-mentioned apparatus 10, is suitably applicable to the cone-beam CT.

As shown in FIG. 6, the data acquiring apparatus 80 uses a large number of line sensors 82 disposed to cover an entire detection area S0, as a solid radiation detector. The line sensors 82 are closely disposed so that the longitudinal direction of each sensor becomes perpendicular to the paper surface, and the line sensors 82 are provided on a circular arc with respect to a radiation source 11.

Data acquiring means 90 generates transmitted-radiation image data, based on a detection signal from each line sensor 82, and acquires an entire detection area quantity of transmitted-radiation image data by collecting each transmitted-radiation image data. Note that it is a matter of course that in using a large number of line sensors in this manner, if the characteristics differ from one another, then it is preferable to correct the characteristics so that equal data can be obtained.

In the above-mentioned data acquiring apparatus 10, an entire detection area quantity of transmitted-radiation image data is acquired by moving each line sensor 12 within each division area. However, the data acquiring apparatus 90 differs in that an entire detection area quantity of transmitted-radiation image data is acquired by collecting each transmitted-radiation image data acquired at each position of disposition without moving each line sensor 82.

When the data acquiring apparatus 80 is applied to the cone-beam CT, the line sensors 82 are handled as a single radiation detector. The operation is the same as the above-mentioned cone-beam CT 1 of FIG. 1, except that the transmitted-radiation image data from the line sensors 82 acquired at the positions of disposition are collected to acquire an entire detection area quantity of transmitted-radiation image data. In forming the three-dimensional image or the fault image of the subject 19, based on an entire detection area quantity of transmitted-radiation image data in each direction of projection output from the data acquiring means 90, the same method as the above-mentioned image processing section 30 can be applied and therefore a description of the operation is omitted.

Thus, if a large number of line sensors are disposed to cover an entire detection area and if the detection signals output from the line sensors are collected, the image of a large area can be formed without using a large-area sensor.

While the present invention has been described with reference to the preferred embodiments thereof, the invention is not to be limited to the details given herein, but may be modified within the scope of the appended claims.

What is claimed is:

1. A method of acquiring transmitted-radiation image data on a subject, by emitting cone radiation from a radiation source toward said subject and by detecting said cone radiation transmitted through said subject with a solid radiation detector, while said radiation source and said solid radiation detector disposed with said subject therebetween are being rotated relatively with respect to said subject;

said method comprising the steps of employing a plurality of line sensors as said solid radiation detector;

dividing an entire detection area for each direction of projection into a plurality of division areas;

disposing each of said line sensors in each of said division area so that each of said line sensors is movable within said division area; and obtaining an entire detection area quantity of transmitted-radiation image data by detecting said cone radiation transmitted through said subject with each of said line sensors, while each of said line sensors is being moved within each of said division areas.

2. A method of acquiring transmitted-radiation image data on a subject, by emitting cone radiation from a radiation source toward said subject and by detecting said cone radiation transmitted through said subject with a solid radiation detector, while said radiation source and said solid radiation detector disposed with said subject therebetween are being rotated relatively with respect to said subject;

said method comprising the steps of constituting said solid radiation detector by a plurality of line sensors physically separately disposed from one another and arranged to cover an entire detection area; and obtaining an entire detection area quantity of transmitted-radiation image data by detecting said cone radiation transmitted through said subject with each said line sensor.

3. The method as set forth in claim 1 wherein substantially the rectilinear propagation component of the radiation, emitted from said radiation source and transmitted through said subject, is only incident on said line sensor.

4. The method as set forth in claim 2, wherein substantially the rectilinear propagation component of the radiation, emitted from said radiation source and transmitted through said subject, is only incident on said line sensor.

5. The method as set forth in claim 1, wherein said detection is performed during the dilation period or contraction period of the heart of said subject in synchronization with heartbeats of said subject.

6. The method as set forth in claim 2, wherein said detection is performed during the dilation period or contraction period of the heart of said subject in synchronization with heartbeats of said subject.

7. An apparatus for acquiring transmitted-radiation image data on a subject, by emitting cone radiation from a radiation source toward said subject and by detecting said cone radiation transmitted through said subject with a solid radiation detector, while said radiation source and said solid radiation detector disposed with said subject therebetween are being rotated relatively with respect to said subject;

said apparatus comprising said radiation source;

a plurality of line sensors employed as said solid radiation detector, each line sensor being disposed so that said line sensor is movable within each of a plurality of division areas formed by dividing an entire detection area;

means for moving each of said line sensors within each of said division areas for each direction of projection; and data acquiring means for acquiring an entire detection area quantity of transmitted-radiation image data by detecting said cone radiation transmitted through said subject with each of said line sensors at each moved position.

8. An apparatus for acquiring transmitted-radiation image data on a subject, by emitting cone radiation from a radiation source toward said subject and by detecting said cone radiation transmitted through said subject with a solid radiation detector, while said radiation source and said solid radiation detector disposed with said subject therebetween are being rotated relatively with respect to said subject;

said apparatus comprising said radiation source;

a plurality of line sensors employed as said solid radiation detector, said plurality of line sensors being physically separately disposed from one another to cover an entire detection area; and data acquiring means for acquiring an entire detection area quantity of transmitted-radiation image data by detecting said cone radiation transmitted through said subject with each said line sensor.

9. The apparatus as set forth in claim 7, wherein said line sensors are provided on a circular arc with respect to said radiation source.

10. The apparatus as set forth in claim 8, wherein said line sensors are provided on a circular arc with respect to said radiation source.

11. The apparatus as set forth in claim 7, further comprising incident-direction control means which causes substantially the rectilinear propagation component of the radiation, emitted from said radiation source and transmitted through said subject, to be only incident on said line sensors.

12. The apparatus as set forth in claim 8, further comprising incident-direction control means which causes substantially the rectilinear propagation component of the radiation, emitted from said radiation source and transmitted through said subject, to be only incident on said line sensors.

13. The apparatus as set forth in claim 9, further comprising incident-direction control means which causes substantially the rectilinear propagation component of the radiation, emitted from said radiation source and transmitted through said subject, to be only incident on said line sensors.

14. The apparatus as set forth in claim 7, further comprising synchronization means which performs said detection during the dilation period or contraction period of the heart of said subject in synchronization with heartbeats of said subject.

15. The apparatus as set forth in claim 8, further comprising synchronization means which performs said detection during the dilation period or contraction period of the heart of said subject in synchronization with heartbeats of said subject.

16. The apparatus as set forth in claim 9, further comprising synchronization means which performs said detection during the dilation period or contraction period of the heart of said subject in synchronization with heartbeats of said subject.

* * * * *